(12) United States Patent
Hirano et al.

(10) Patent No.: US 8,701,488 B2
(45) Date of Patent: Apr. 22, 2014

(54) ELECTRONIC COMPONENT ANALYZING APPARATUS AND METHOD

(75) Inventors: Yoshikazu Hirano, Kawasaki (JP); Mitsunori Abe, Kawasaki (JP); Takashi Fukuda, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 214 days.

(21) Appl. No.: 13/172,159

(22) Filed: Jun. 29, 2011

(65) Prior Publication Data

US 2012/0017679 A1 Jan. 26, 2012

(30) Foreign Application Priority Data

Jul. 26, 2010 (JP) ................................. 2010-166812

(51) Int. Cl.
*G01P 15/00* (2006.01)
*G01M 7/00* (2006.01)

(52) U.S. Cl.
USPC ....................... 73/514.01; 73/12.01; 73/12.09

(58) Field of Classification Search
USPC .......... 73/514.01, 12.01, 12.04, 12.09, 12.11, 73/11.01
See application file for complete search history.

(56) References Cited

U.S. PATENT DOCUMENTS

| | | | |
|---|---|---|---|
| 6,690,284 B2* | 2/2004 | Ohno et al. | 340/679 |
| 6,870,525 B2* | 3/2005 | Kawabata et al. | 345/102 |
| 6,906,546 B2* | 6/2005 | Tanioka et al. | 324/750.1 |
| 7,412,870 B2* | 8/2008 | Brankov | 73/12.11 |
| 7,500,378 B2* | 3/2009 | Tsai et al. | 73/12.09 |
| 8,375,804 B2* | 2/2013 | Su et al. | 73/842 |
| 2002/0080041 A1* | 6/2002 | Ohno et al. | 340/679 |
| 2004/0100297 A1* | 5/2004 | Tanioka et al. | 324/765 |
| 2007/0284042 A1 | 12/2007 | Yamamoto | |
| 2009/0139303 A1* | 6/2009 | Zhang et al. | 73/12.09 |

FOREIGN PATENT DOCUMENTS

| | | |
|---|---|---|
| JP | 6-080159 | 11/1994 |
| JP | 09-264854 | 10/1997 |
| JP | 2001-244307 A | 9/2001 |
| JP | 2006-078384 | 3/2006 |
| JP | 2007-335447 A | 12/2007 |
| JP | 2009-025218 | 2/2009 |
| JP | 2009-229163 | 10/2009 |

OTHER PUBLICATIONS

Notification of Reasons for Refusal dated Feb. 12, 2014 corresponding to Japanese Patent Application No. 2010-166812 and English translation thereof.

* cited by examiner

*Primary Examiner* — Helen Kwok
(74) *Attorney, Agent, or Firm* — Squire Sanders (US) LLP

(57) ABSTRACT

An electronic component analyzing apparatus is provided with a fixing part configured to hold a substrate to which an electronic component is soldered; a gripper configured to grip the electronic component; a transmission part coupled to the gripper, and configured to transmit an external force to the gripper as a force acting in a direction away from the substrate; and a support part configured to pivotally support the transmission part.

18 Claims, 7 Drawing Sheets

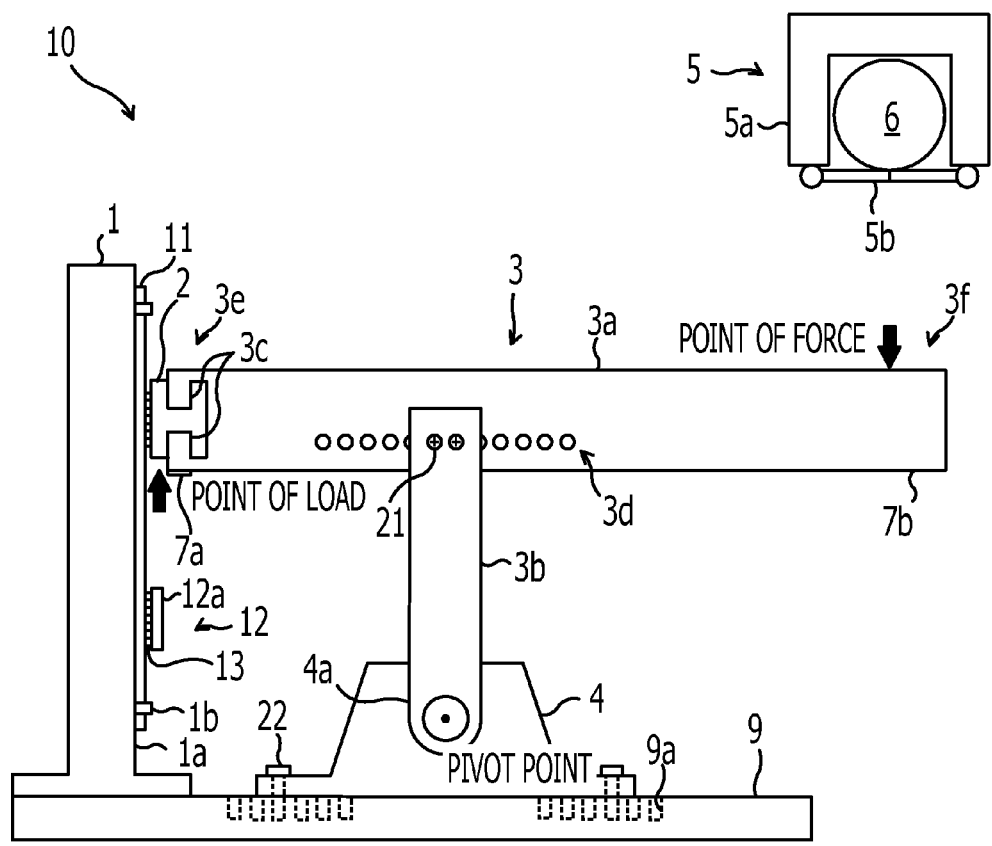
FIG. 1A
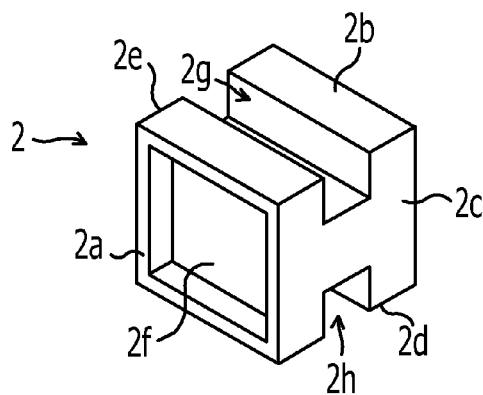
FIG. 1B
FIG. 1C

ELECTRONIC COMPONENT ANALYZING APPARATUS AND METHOD

CROSS-REFERENCE TO RELATED APPLICATION

This application is based upon and claims the benefit of priority of Japanese Patent Application No. 2010-166812, filed on Jul. 26, 2010, the entire contents of which are incorporated herein by reference.

FIELD

The embodiments discussed herein relate to an electronic component analyzing apparatus and method.

BACKGROUND

To date, temperature cycling tests have been conducted to analyze joint quality and reliability of electronic components which are soldered to printed wiring boards. During the temperature cycling tests, thermal stresses are induced on a solder joint by repeatedly changing the temperature. In the temperature cycling test, the quality and reliability of a solder joint may be estimated by checking whether any cracks have formed in the solder joint and/or by checking the depth, the growth, the location, etc. of the cracks. In a typical method of analyzing cracks, after the solder joint is cut perpendicular to the printed wiring board and then the cut surface is polished, the polished cut surface is observed by a Scanning Electron Microscope (SEM), for example.

However, according to the above-mentioned analyzing method, only cracks that appear on the cut surface may be observed. That is, for example, when a plurality of solder joints is provided over a single electronic component, it is desirable for a plurality of cut surfaces to be prepared. Thus, the amount of time and effort spent in cutting the solder joint and polishing the cut surface may be significant, and the operation efficiency may be poor. Furthermore, for example, in case of a crack spreading out parallel to the printed wiring board, it is difficult to observe the overall feature of the crack.

In Japanese Laid-Open Patent Publication No. 9-264854, a method of observing the torn surface of the solder joint by tearing off the solder joint along the expanded face of the crack is discussed.

However, it is difficult to maintain the original condition of a crack while tearing off the solder joint. For example, using a tensile strength testing device to pull off an electronic component from a printed wiring board may cause ductile fracture in the solder joints and deformation of the solder joints and cracks therein. Furthermore, deformation of the solder joints and cracks may cause additional scratches and cracks. As a result, it may be difficult to distinguish a crack caused by thermal stress from one caused by physical stress.

Thus, according to the above-mentioned analyzing method with a tensile strength testing device, enhancing the accuracy of analyzing the cut surface is difficult because tearing-off traces may be left over the cut surface.

SUMMARY

According to an embodiment of the invention, an electronic component analyzing apparatus is provided with a fixing part configured to hold a substrate to which an electronic component is soldered; a gripper configured to grip the electronic component; a transmission part coupled to the gripper, and configured to transmit an external force to the gripper as a force acting in a direction away from the substrate; and a support part configured to pivotally support the transmission part.

It is to be understood that both the foregoing general description and the following detailed description are exemplary and explanatory, and are not restrictive of the invention.

BRIEF DESCRIPTION OF THE DRAWINGS

FIG. 1A is a side view of a configuration of an electronic component analyzing apparatus according to Embodiment 1;

FIG. 1B is a perspective view of a gripper of the electronic component analyzing apparatus in FIG. 1A;

FIG. 1C is a perspective view of an electronic component to be analyzed by the electronic component analyzing apparatus in FIG. 1A;

DESCRIPTION OF EMBODIMENTS

Figure 2A:
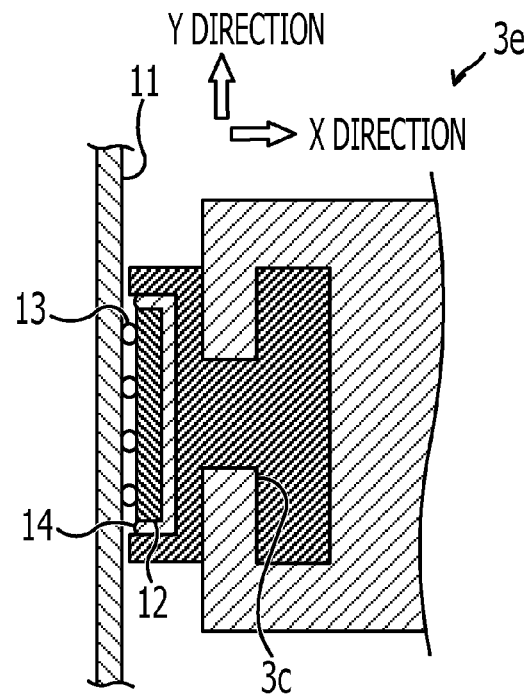
FIG. 2A is an enlarged sectional view of the gripper of the electronic component analyzing apparatus in FIG. 1A.

Embodiments of an electronic component analyzing apparatus and method are described below with reference to the accompanying drawings.

FIGS. 1A, 1B, and 1C are diagrams respectively illustrating an example of a configuration of an analyzing apparatus 10, a gripper 2, and an electronic component 12. The analyzing apparatus 10 is configured to pull off the electronic component 12 from a substrate 11 (e.g., a printed wiring board), where the electronic component 12 is attached to the substrate 11 via solder joints. The analyzing apparatus 10 is used, for example, to check and analyze the quality and reliability of solder joints to which thermal stresses have been applied in a temperature cycling test.

In FIG. 1C, the electronic component 12 arranged for example in a ball grid array (BGA) package, made by arranging solder bumps in an array pattern (an intersecting grid-like pattern), is illustrated as an example of an electronic component being pulled off. The electronic component 12 in this example is a BGA package having a plurality of solder bumps 13 as solder joints which are arranged over one surface of a resin seal 12a. Integrated circuit (IC) chips or large scale integration (LSI) chips are embedded in the resin seal 12a.

The analyzing apparatus 10 may include a fixing part 1, the gripper 2, a transmission part 3, a support part 4, and an impact force applying unit 5 to tear off the plurality of solder bumps 13 at once by pulling off the electronic component 12 from the substrate 11.

The fixing part 1 securely holds the substrate 11 with respect to a platform 9. For example, the platform 9 is placed horizontally on a desk, and the fixing part 1 is fixed upright to the platform 9. As illustrated in FIG. 1A, the platform 9 and the fixing part 1 may be arranged in an L-shape. A band-like clamp 1b is provided on a surface is of the fixing part 1, and the substrate 11 is securely held by the clamp 1b of the fixing part 1. Alternatively, the substrate 11 may be held on the surface is of the fixing part 1 through positioning screws.

The gripper 2 is a member to grip the electronic component 12 mounted on the substrate 11. As illustrated in FIG. 1B, the gripper 2 in this example has a rectangular parallelepiped shape with concave (recess or groove) portions on three sides thereof. On a first surface 2a of the gripper 2, a recess 2f is formed to fit the outline of the corresponding electronic component 12. Hereinafter, the lateral surfaces adjacent to the first surface 2a of the gripper 2 are each referred to as a second surface 2b, a third surface 2c, a fourth surface 2d, and a fifth surface 2e. The second surface 2b and the fourth surface 2d, which are parallel to each other, each includes a locking groove 2g and a locking groove 2h passing across the third surface 2c to the fifth surface 2e. The locking grooves 2g and 2h are formed parallel to the first surface 2a. That is, the gripper 2 is extruded in a direction perpendicular to the H-shaped third surface 2c, and the recess 2f is formed over the first surface 2a.

The transmission part 3 includes a lever 3a and a strut 3b. The lever 3a is a bar-like member whose one end 3e is coupled to the gripper 2. In case that the gripper 2 is separately formed from the transmission part 3, a projection 3c is provided on one end 3e to fit into the locking grooves 2g and 2h of the gripper 2. Thus, the gripper 2 may be detachably affixed to the lever 3a. Alternatively, the transmission part 3 and the gripper 2 may be integrally formed with a unitary structure. Thus, it is preferable for the transmission part 3 and the gripper 2 to be continuously connected.

The strut 3b is a bar-like member whose upper end portion is affixed to the lever 3a while the lower end portion is pivotally supported by the support part 4. The support part 4 is a member to support the strut 3b along a rotation axis 4a so that the strut 3b is swingably moved with respect to the platform 9. Likewise, the transmission part 3 is supported by the strut 3b so that the transmission part 3 is swingably moved about the rotation axis 4a.

A plurality of screw holes 3d is arranged on the lever 3a along an extension direction of the lever 3a. The upper end portion of the strut 3b may be affixed with respect to the screw holes 3d via given fasteners 21. Thus, the junction location between the lever 3a and the strut 3b may be adjustable along the extension direction of the lever 3a.

Similarly, another screw holes 9a is arranged on the platform 9 along the extension direction of the lever 3a. The support part 4 may be affixed with respect to the screw holes 9a via given fasteners 22. Thus, the junction location between the support part 4 and the platform 9 may also be adjustable along the extension direction of the lever 3a. By cooperation with the fasteners 21 and 22, the screw holes 3d and 9a may function as adjustment mechanisms by which the support location of the transmission part 3 with respect to the support part 4 is adjustable.

The strut 3b supports the lever 3a so as to level both one end 3e and the other end 3f (hereinafter respectively referred to as "first end 3e" and "second end 3f") of the lever 3a. Thus, the lever 3a is oriented perpendicular to the substrate 11.

The impact force applying unit 5 applies external force to the transmission part 3. The impact force applying unit 5 includes a main body 5a housing a steel ball 6, and a gate 5b therein. The gate 5b may be opened and closed from the bottom surface of the main body 5a. The impact force applying unit 5 applies impact force to the second end 3f of the lever 3a by letting the steel ball 6 drop. The term "impact force" used herein refers to the force generated by the impact load.

The transmission part 3 transmits external force to the gripper 2 and functions as a lever that acts on the electronic component 12 to move in a direction away from the substrate 11. As illustrated in FIG. 1A, the point where impact force is applied by the steel ball 6 functions as the point of force in the principle of leverage. The center of rotation of the rotation axis 4a functions as the pivot point, and the solder bumps 13 located between the substrate 11 and the electronic component 12 may function as the point of load. The ratio of the distance between the point of force and the pivot point, a length $L_1$, to the distance between the point of load and the pivot point, a length $L_2$, is proportionate to the ratio of the amount of force acted on the point of load to the amount of force applied to the point of force. Thus, in order to increase the impact force, it is preferable to set the length $L_1$ longer than the length $L_2$. In contrast, in order to reduce the impact force because the external force is excessively high, it is preferable to set the length $L_1$ shorter than the length $L_2$.

Thus, when pulling off the electronic component 12 from the substrate 11, the pivot point, the point of force, and the point of load are located respectively in the support part 4, the transmission part 3, and the gripper 2 of the analyzing apparatus 10. That is, the support part 4 functions as a pivot point member, the transmission part 3 functions as a force point member, and the gripper 2 functions as a load point member.

For example, when the gate 5b of the impact force applying unit 5 is opened and the steel ball 6 drops, the impact force in a downward direction is applied to the second end 3f of the lever 3a. Due to the impact force, the transmission part 3 swings about the rotation axis 4a, and thus the impact force is transmitted to the first end 3e of the lever 3a, and the gripper 2. Accordingly, the gripper 2 intends to rotate about the rotation axis 4a, and thus, a force vector parallel to the substrate 11 and a force vector perpendicular to the substrate 11 are generated in the gripper 2.

A pair of acceleration sensors, an acceleration sensor 7a and an acceleration sensor 7b are provided over the lever 3a. The acceleration sensor 7a (hereinafter referred to as "first sensor 7a") is provided in the vicinity of the first end 3e of the lever 3a and the gripper 2. Also, the acceleration sensor 7b (hereinafter referred to as "second sensor 7b") is provided in the vicinity of the second end 3f of the lever 3a. The first sensor 7a detects the acceleration that acts on the electronic component 12 when the electronic component 12 is pulled off from the substrate 11. The second sensor 7b detects the acceleration that acts on the second end 3f of the lever 3a, which is caused by external force.

FIG. 2A is an enlarged sectional view of the gripper 2. The space between the recess 2f of the gripper 2 and the electronic component 12 is filled with an adhesive 14. The adhesive 14 may be omitted, or the adhesive 14 may be applied to only the back surface (the surface opposite to the surface with solder bumps) of the electronic component 12 in accordance with the junction strength, etc. of the solder bumps 13. Alternatively, the adhesive 14 may be applied to only the side surfaces of the electronic component 12.

Figure 2B:
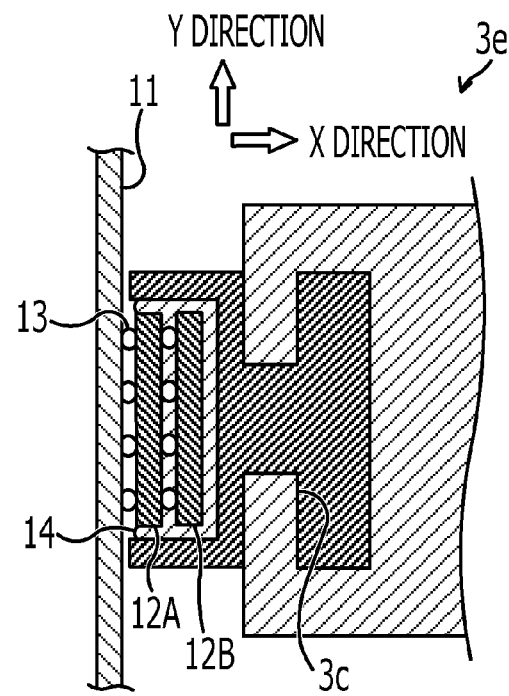
FIG. 2B is an enlarged sectional view of the gripper of the electronic component analyzing apparatus in FIG. 1A.

As illustrated in FIG. 2B, in the case of the electronic component 12 including a plurality of semiconductors such as stacked-up multi-chip modules, the adhesive 14 may be also applied between a lower component 12A and an upper component 12B, in addition to the back surface and/or the side surfaces of the electronic component 12, to pull off the solder joint from the substrate 11. Thus, the upper component 12B may be suppressed from being pulled off from the lower component 12A.

Figure 3:
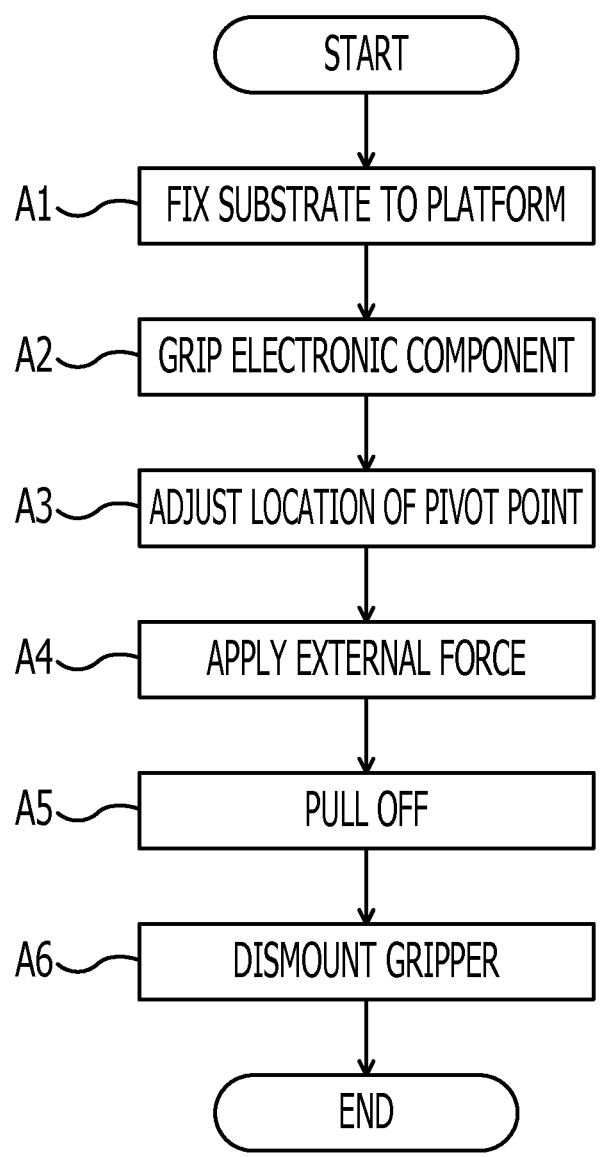
FIG. 3 is a flowchart for explaining analyzing procedures using the electronic component analyzing apparatus in FIG. 1A.

FIG. 3 is a flowchart explaining an example of procedures to pull off the electronic component 12.

In operation A1, the substrate 11 is placed between the surface is of the fixing part 1 and the clamp 1b, and is affixed to the fixing part 1. The affixation position of the substrate 11 is set so that the electronic component 12 to be analyzed is opposed to the lever 3a when the lever 3a is oriented horizontally.

In operation A2, the back surface and the side surfaces of the electronic component 12 are gripped by the recess 2f of the gripper 2. For example, the back surface of the electronic component 12 may be affixed to the gripper 2 by applying the adhesive 14 on the recess 2f of the gripper 2. Alternatively, the adhesive 14 may be filled in the space between the recess 2f and the electronic component 12.

This allows the electronic component 12 to be firmly gripped by the gripper 2. Also, the gripper 2 is attached to the first end 3e of the lever 3a. Consequently, the electronic component 12 is gripped by the first end 3e of the transmission part 3 through the gripper 2.

In operation A3, the connection location between the strut 3b and the lever 3a is adjusted. Also, the affixation location of the support part 4 to the platform 9 is adjusted. These adjustments performed in operation A3 may change the ratio of the length $L_1$ to the length $L_2$, and thus the amount of force that acts on the point of load may be controlled.

In operation A4, the gate 5b of the impact force applying unit 5 is opened in a state that the electronic component 12 is gripped by the transmission part 3. When the steel ball 6 drops toward the transmission part 3, impact force in accordance with the mass and the fall length of the steel ball 6 is applied to the second end 3f of the lever 3a. Thus, for example, the transmission part 3 swings about the rotation axis 4a in a clockwise direction of FIG. 1A.

The amount of impact force applied to the point of force is detected by the second sensor 7b. The amount of impact force detected by the second sensor 7b is input to a controller or a computer, which is not illustrated. The detected amount of impact force may be referred to when setting the amount of impact force to be applied in a subsequent operation A4 by the impact force applying unit 5.

In response to the clockwise movement of the transmission part 3, impact force consequently acts on the solder bumps 13 of the electronic component 12 in a direction away from the substrate 11 in operation A5.

As illustrated in FIG. 2A, due to the impact force along an X direction acting perpendicular to the surface of the substrate 11, and due to the impact force along a Y direction acting parallel to the surface of the substrate 11, shear stress is generated inside the solder bumps 13. As a result, the solder bumps 13 are torn off and the electronic component 12 is pulled off from the substrate 11. When vulnerable areas such as cracks or scratches already exist inside the solder bumps 13, a torn surface is formed with cracks and scratches as an interfacial surface. Each of the pulled-off solder bumps 13 remains adhered to the electronic component 12, and the arrangement of each of the solder bumps 13 remains unchanged even after the solder bumps 13 have been pulled off.

The amount of impact force that acts on the point of load is detected by the first sensor 7a. The detected amount of impact force is input to a controller or a computer, which is not illustrated, and is used to figure out the joint strength of the solder bumps 13. The detected amount of impact force may be referred to when setting the amount of impact force to be applied in a subsequent operation A4 by the impact force applying unit 5.

Figure 4A:
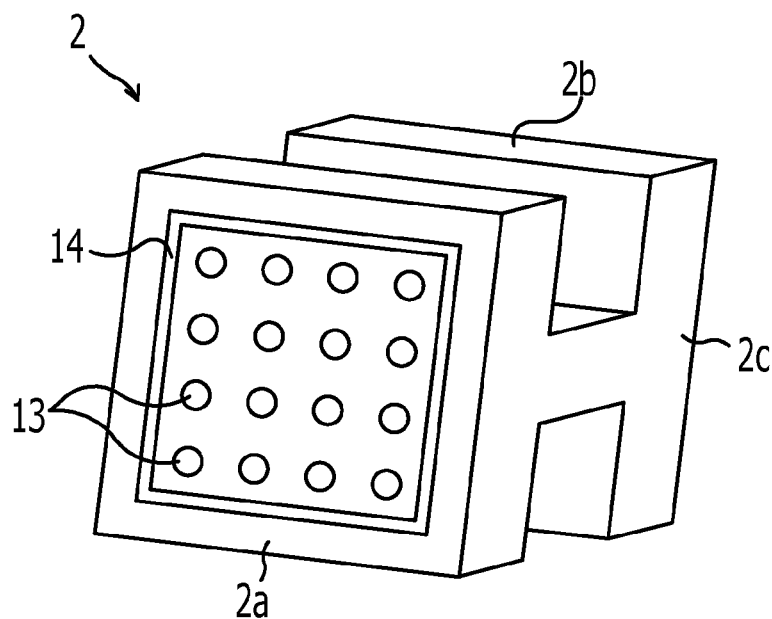
FIG. 4A is a front view of the gripper after a plurality of solder joints of the electronic component has been pulled off using the electronic component analyzing apparatus in FIG. 1A and after the gripper has been analyzed.
Figure 4B:
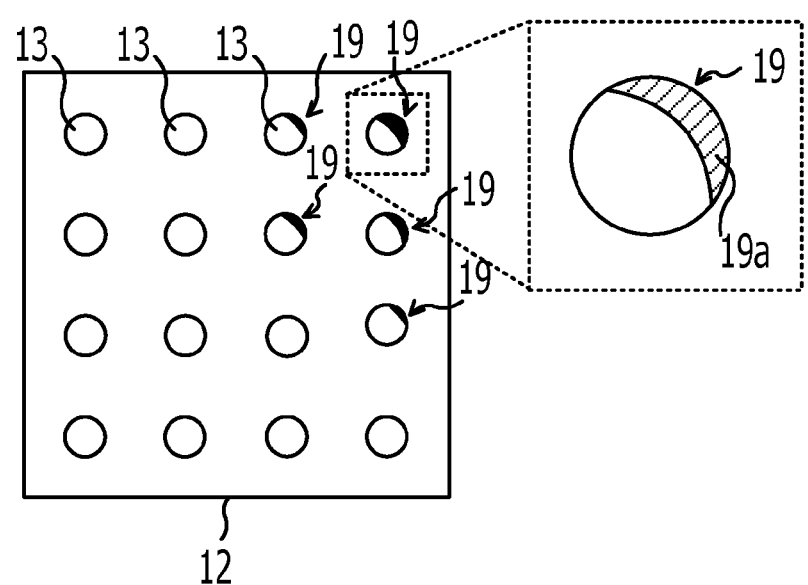
FIG. 4B is a partial enlarged view of the gripper after the solder joints of the electronic component have been pulled off using the electronic component analyzing apparatus in FIG. 1A and after the gripper has been analyzed.

In operation A6, the gripper 2 gripping the electronic component 12 therein is dismounted from the lever 3a. The gripper 2 is placed in a sample chamber of a Scanning Electron Microscope (SEM), and the torn surfaces of the solder bumps 13 may be analyzed. As illustrated in FIG. 4A, parts of the torn-off solder bumps 13 remain adhered to the electronic component 12. As illustrated in FIG. 4B, cracks 19 and/or scratch marks remain over the torn surface of the solder bumps 13.

For example, when a crack 19 is observed in parts of the torn surfaces of the respective solder bumps 13 arranged in an array pattern, it may be assumed that the crack 19 was caused by a rupture during a temperature cycling test. By observing the direction of the stripes in a striation 19a (streak) remaining over the surfaces of the cracks 19, it may be assumed that thermal stress has been applied in a direction perpendicular to the stripes. Also, by observing the pitch between the stripes of the striation 19a, the amount of thermal stress may be estimated.

Furthermore, by observing the distribution of the cracks 19 according to this analyzing method, bias in the strength of the resin seal 12a of the electronic component 12 and bias in the joint strength of the solder bumps 13 may be estimated. For example, as illustrated in FIG. 4B, when the cracks 19 are concentrated on the upper right portion of the electronic component 12, it may be assumed that the strength of the upper right portion of the electronic component 12 may be weaker as compared to other portions of the electronic component 12. Incidentally, by observing the growth of the cracks 19, it may be assumed that the rupture may have started at the upper right portion of the electronic component 12 and developed. Furthermore, the areas of the cracks 19 and/or the area ratio of the cracks 19 to the joint areas of the solder bumps 13 may be measured, and the durability (lifetime) of the solder bumps 13 to thermal stress may be estimated.

The above-described estimates may be trusted when the arrangement of each of the solder bumps 13 and the relative position between the resin seal 12a and the corresponding solder bumps 13 remain unchanged even after the solder bumps 13 have been pulled off from the substrate 11.

Thus, by pulling off the electronic component 12 from the substrate 11 using the principle of leverage (that is, by causing the transmission part 3 to swing about the rotation axis 4a when external force is applied), the force transmitted to the gripper 2 may be controlled with ease to increase or decrease. As a result, the electronic component 12 may be pulled off from the substrate 11 with a desirable force. Thus, deformation of the torn surfaces and formation of scratches accompanying a rupture may be reliably suppressed.

When a pulling-off speed of the electronic component 12 is slow, ductile fracture may occur in the torn surfaces of the solder bumps 13. Ductile fracture is a phenomenon in which the solder bumps 13 become ruptured when the solder bumps 13 have been plastically pulled apart, and deformation that is dependent on the pulling-off speed remains over the torn surfaces. Thus, for example, in a method where external force is applied gradually, the torn surfaces of the solder bumps 13 may be deformed, and the cut surface may not be analyzed accurately. The above-described problem becomes prominent when a tensile strength testing device in which the velocity is increased from a rest state (a state where the initial velocity is zero), is used.

According to Embodiment 1, to solve the above-mentioned problem, impact force is applied to the transmission part 3 to increase the initial velocity of the movement of the gripper 2, and ductile fracture may be suppressed in the solder bumps 13. Thus, deformation of the torn surfaces and/or occurrence of scratches accompanying a rupture may be reliably suppressed. Specifically, when compared with using a tensile strength testing device, deformation of the cracks 19 remaining over the torn surfaces may be reliably reduced, and the accuracy of analysis may be enhanced.

Furthermore, portability may be enhanced by dismounting the gripper 2 from the transmission part 3, together with the electronic component 12 that has been pulled off from the substrate 11. Thus, for example, it may become easier to place the electronic component 12 in the sample chamber of the SEM. Also, by exchanging the grippers 2, the electronic components 12 of different sizes may be easily accommodated, and versatility may be expanded.

In addition, in Embodiment 1, the connection location of the lever 3a and the strut 3b may be changed, and the affixation location of the support part 4 to the platform 9 may also be changed. That is, by enabling the support location of the transmission part 3 to be changed with respect to the support part 4, the amount and direction of force that acts in the vicinity of the gripper 2 may be controlled with ease despite a specified amount of the external force. For example, by shifting the location of the pivot point closer to the point of load, the ratio of $L_1$ to $L_2$ becomes larger, and thus the impact force that acts on the solder bumps 13 of the electronic component 12 may be increased. By shifting the location of the pivot point closer to the point of force, the ratio of $L_1$ to $L_2$ becomes smaller, and the impact force that acts on the solder bumps 13 may be reduced. Thus, the desirable location of the pivot point may be pursued in accordance with the joint strength of the solder bumps 13, the strength of the resin seal 12a of the electronic component 12, the strength of the adhesive 14, etc.

Also, in Embodiment 1, since the first sensor 7a and the second sensor 7b are provided in the vicinity of the point of load and the point of force, the amount of impact force that is applied by actual external force, and the amount of impact force that acts on the solder bumps 13 of the electronic component 12 may be accurately figured out. By referring to these parameters, the joint strength of the solder bumps 13 may be estimated, and the above-mentioned desirable location of the pivot point may be set more accurately.

Since the back surface of the electronic component 12 is adhesively attached to the recess 2f of the gripper 2 with the adhesive 14, the grip force in gripping the electronic component 12 may be enhanced, and thus the electronic component 12 may be reliably pulled off from the substrate 11. Furthermore, when the adhesive 14 is filled in the space between the recess 2f and the electronic component 12, the grip force in gripping the electronic component 12 may be enhanced further. As illustrated in FIG. 2B, even when a plurality of semiconductors is stacked in the electronic component 12, the force acts on solder joints toward the substrate 11, and thus the electronic component 12 may be reliably pulled off from the substrate 11 without separating the stacked semiconductors.

Also, by simultaneously pulling off the multiple solder joints of the electronic component 12, the distribution and extent of the cracks 19 may be observed two-dimensionally. Furthermore, the arrangement of the solder bumps 13 and the relative position between the solder bumps 13 and the resin seal 12a may be reliably maintained even after the solder bumps 13 have been pulled off. Therefore, bias in the strength of the resin seal 12a and bias in the joint strength of the solder joints may be estimated.

Figure 5A:
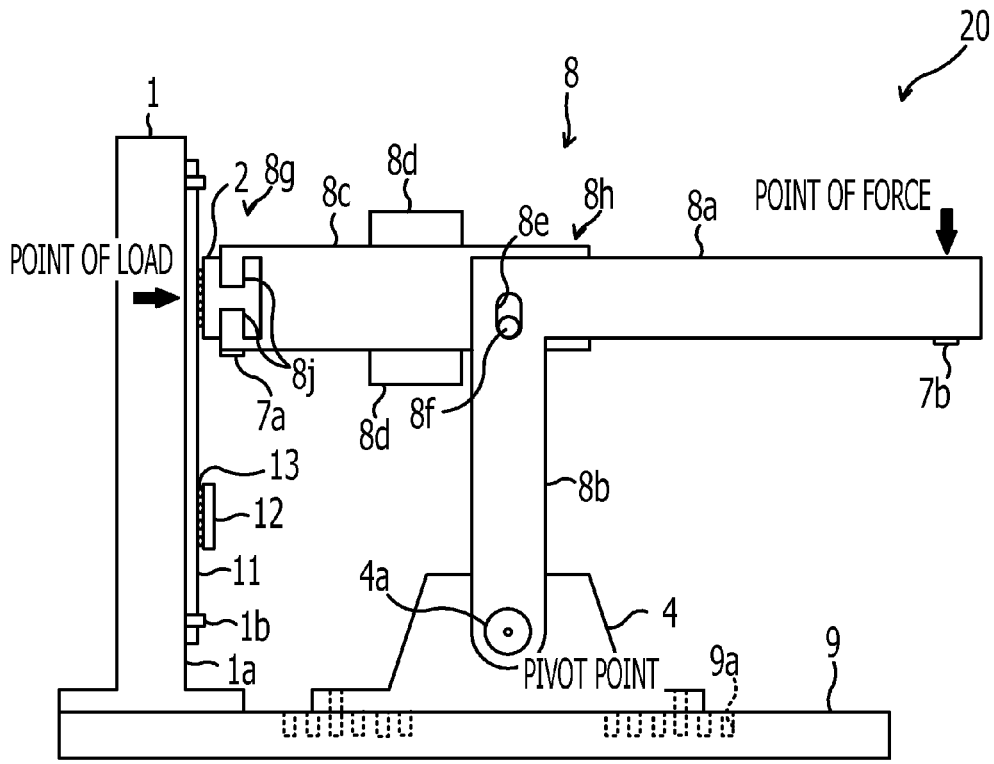
FIG. 5A is a side view of a configuration of an electronic component analyzing apparatus according to Embodiment 2 before a plurality of solder joints is pulled off.
Figure 5B:
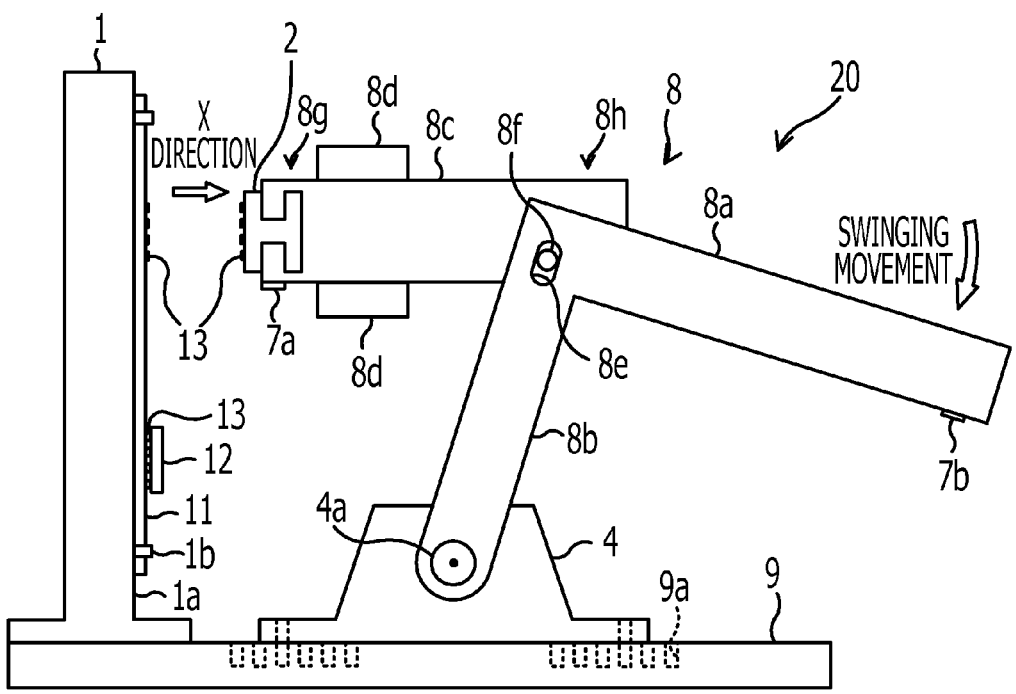
FIG. 5B is a side view of the configuration of the electronic component analyzing apparatus according to Embodiment 2 after the solder joints have been pulled off.

An analyzing apparatus 20 in Embodiment 2 is described with reference to FIGS. 5A and 5B. In FIGS. 5A and 5B, the same reference numerals are given to similar elements as those used in the above-mentioned Embodiment 1. In FIGS. 5A and 5B, an impact force applying unit is not illustrated for the sake of simplicity. The analyzing apparatus 20 includes a fixing part 1, a gripper 2, a transmission part 8, a support part 4, and the impact force applying unit (not illustrated).

The transmission part 8 includes a lever 8a, a strut 8b, a rectilinear movement member 8c, and a guide member 8d. The lever 8a and the strut 8b correspond to the lever 3a and the strut 3b in Embodiment 1. The lever 8a is a bar-like member, and an external force directly acts on the lever 8a. The strut 8b is a bar-like member with the upper end portion affixed to the lever 8a. The lower end portion of the strut 8b is pivotally supported by the support part 4. The lever 8a is swingably moved about a rotation axis 4a through the strut 8b. Also, an elongated hole 8e is formed in the lever 8a along the radiation direction with respect to the rotation axis 4a.

The rectilinear movement member 8c has a box-like shape. The gripper 2 is coupled to one end 8g of the rectilinear movement member 8c, and the top surface and the bottom surface of the rectilinear movement member 8c are formed to be smooth. The rectilinear movement member 8c includes a first projection 8j provided on one end 8g thereof. The first projection 8j fits into a locking groove 2g and 2h of the gripper 2. Thus, the gripper 2 is removably affixed to the rectilinear movement member 8c through the first projection 8j. On the other hand, a second projection 8f is provided on the other end 8h of the rectilinear movement member 8c.

The second projection 8f is engaged and slides in the elongated hole 8e. Through the engagement between the second projection 8f and the elongated hole 8e, the rectilinear movement member 8c and the lever 8a are connected. In response to a swing movement of the lever 8a and the strut 8b, the second projection 8f slides inside the elongated hole 8e.

The guide member 8d is affixed to a platform 9, and slidingly contacts the top surface and the bottom surface of the rectilinear movement member 8c. The guide member 8d guides the rectilinear movement member 8c to vertically move with respect to a substrate 11. The guide member 8d, the elongated hole 8e, and the second projection 8f function as a movement conversion part, which assists the rectilinear movement in a direction perpendicular to the substrate 11, based on the swing movement of the lever 8a and the strut 8b.

When pulling off an electronic component 12 from the substrate 11 with use of the analyzing apparatus 20, the pivot point, the point of force, and the point of load in the principle of leverage are respectively located in the support part 4, the transmission part 8, and the gripper 2. That is, the support part 4 functions as a pivot point member, the transmission part 8 as a force point member, and the gripper 2 as a load point member.

On the other hand, assuming that the engagement portion of the second projection 8f and the elongated hole 8e functions as the point of load, the lever 8a and the strut 8b function as the force point members. In this case, an amount of impact force that acts on the engagement portion is substantially the same with an amount of pulling-off force applied to the electronic component 12.

When impact force is applied to the point of force of the transmission part 8, which is illustrated in FIG. 5A, the lever 8a and the strut 8b swing about the rotation axis 4a as illustrated in FIG. 5B. The elongated hole 8e moves in an arc-like path and the second projection 8f, which is engaged in the elongated hole 8e, moves along the elongated hole 8e in a clockwise direction. Since the movement of the rectilinear movement member 8c is guided to vertically move with respect to the substrate 11, the second projection 8f slides inside the elongated hole 8e, and thus the rectilinear movement member 8c moves linearly in a direction away from the substrate 11. Consequently, the pulling-off force to the electronic component 12 acts only in an X direction as illustrated in FIG. 5B.

A plurality of cracks 19 that has occurred on a plurality of solder bumps 13 in the temperature cycling test may have a crack width of several or several tens of micrometers (µm). The cracks are formed approximately parallel to the substrate 11. For example, when the size of the solder joint of the electronic component 12 is 20 millimeters (mm), to tear off the solder bumps 13 without causing scratches over the surfaces of the cracks 19, an allowable inclination angle of the electronic component 12 with respect to a vertical line of the substrate 11 is approximately 0.8 degrees or less. Since the allowable inclination angle becomes smaller as the width of the crack 19 becomes smaller, it is desired for the direction in which the force acts on the electronic component 12 when pulling off the electronic component 12 from the substrate 11, to be perpendicular with a high accuracy.

According to Embodiment 2, because the swing movement of the lever 8a and the strut 8b may be converted into the rectilinear movement, the direction in which force acts on the electronic component 12 to pull off the electronic component 12 from the substrate 11 becomes perpendicular to the substrate 11 with a high accuracy, and thus deformation of the torn surfaces and formation of scratches accompanying a rupture may be reliably suppressed. Consequently, the cut surfaces may be analyzed accurately.

Also, since the guide member 8d slidingly guides the rectilinear movement member 8c, the direction of the force that acts on the electronic component 12 when pulling off the electronic component 12 from the substrate 11 may become further kept perpendicular to the substrate 11. Thus, deformation of the torn surfaces and formation of scratches accompanying a rupture may be further suppressed.

Figure 6A:
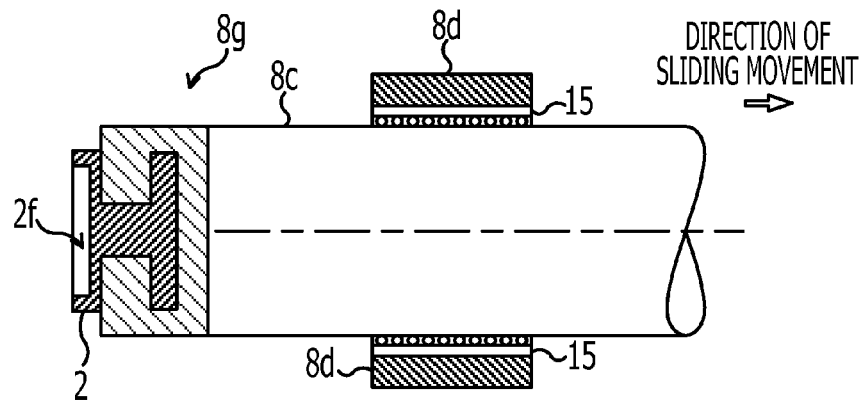
FIGS. 6A to 6C illustrate modified examples of a guide member in FIG. 5A.
Figure 6B:
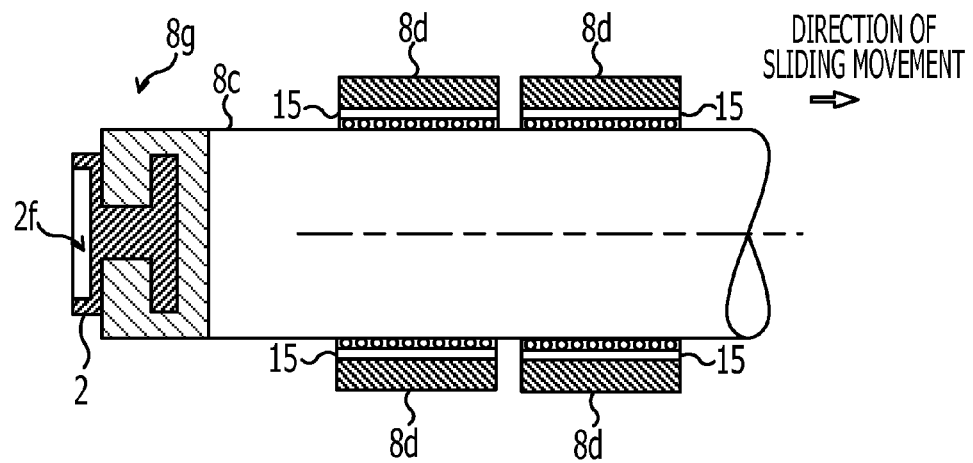
Figure 6C:
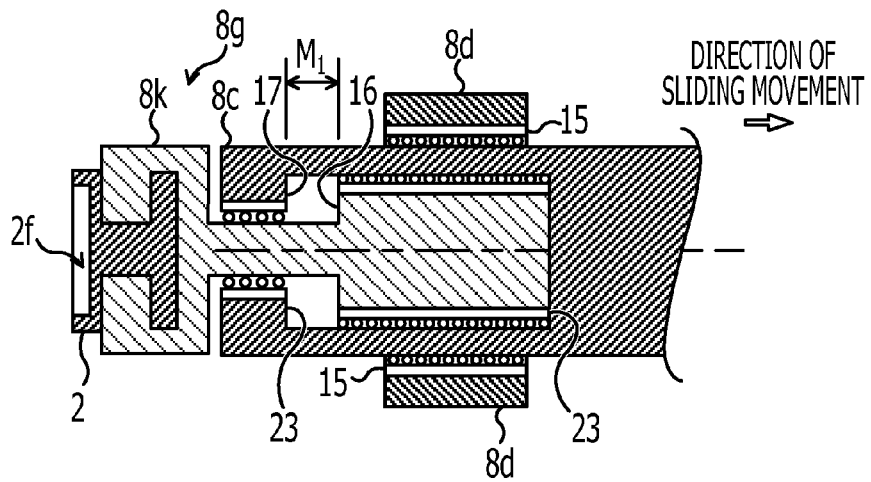

FIGS. 6A, 6B, and 6C illustrate modified examples of the guide member 8d. The modified guide member 8d in FIG. 6A includes a bearing 15 interposed between the rectilinear movement member 8c and the guide member 8d. The bearing 15 may be, for example, a ball bearing or a roller bearing. Alternatively, a shaft-like or ball-like skid may be used.

The bearing or skid structure may reduce the frictional resistance between the guide member 8d and the rectilinear movement member 8c. Thus, the impact force transmitted to the electronic component 12 may be increased. That is, when the impact force used in pulling off the electronic component 12 is substantially unchanged, the amount of impact force applied by the impact force applying unit 5 may be reduced, and thus the configuration of the impact force applying unit 5 may become downsized and simplified.

Another modified guide member 8d in FIG. 6B is provided over a plurality of locations along the direction in which the rectilinear movement member 8c moves. By increasing the contact area between the rectilinear movement member 8c and the guide member 8d, the angle deviation in a moving direction of the rectilinear movement member 8c may be further suppressed, and thus the direction of the force that acts on the electronic component 12 when pulling off the electronic component 12 from the substrate 11 may become further kept perpendicular to the substrate 11.

It is preferable to broadly set the distance between the adjacent guide members 8d when arranging the plurality of guide members 8d. Since the frictional resistance may be increased due to the plurality of guide members 8d and bearings 15, it is preferable to increase the amount of impact force applied from the impact force applying unit 5.

FIG. 6C illustrates yet another modified example of the guide member 8d. In addition to the guide member 8d of FIG. 6A, a leading end part 8k is further provided. The leading end part 8k is separately formed from the rectilinear movement member 8c. The gripper 2 is coupled to one end of the leading end part 8k, and the other end of the leading end part 8k is inserted inside the rectilinear movement member 8c. The other end of the leading end part 8k may be slidingly moved inside the rectilinear movement member 8c. The movement direction of the leading end part 8k is substantially the same with that of the rectilinear movement member 8c.

The leading end part 8k has a first abutting surface 16, which is perpendicular to the movement axis of the leading end part 8k. On the other hand, the rectilinear movement member 8c includes a second abutting surface 17 thereinside, which is opposed to the first abutting surface 16. The first abutting surface 16 and the second abutting surface 17 are positioned parallel to each other with a gap of a given length $M_1$. A bearing 23 is interposed between the inserted part of the leading end part 8k and the rectilinear movement member 8c.

Due to the above-described configuration of the leading end part 8k, when the rectilinear movement member 8c slides the given length $M_1$, the impact force may be transmitted from the second abutting surface 17 to the first abutting surface 16. As a result, the leading end part 8k starts to slide in a direction (along the moving axis) perpendicular to the surface of the substrate 11 with an enhanced initial velocity. Consequently, ductile fracture in the solder bumps 13 may be suppressed, and thus, deformation of the torn surfaces and formation of scratches accompanying a rupture may be reliably reduced.

Figure 7:
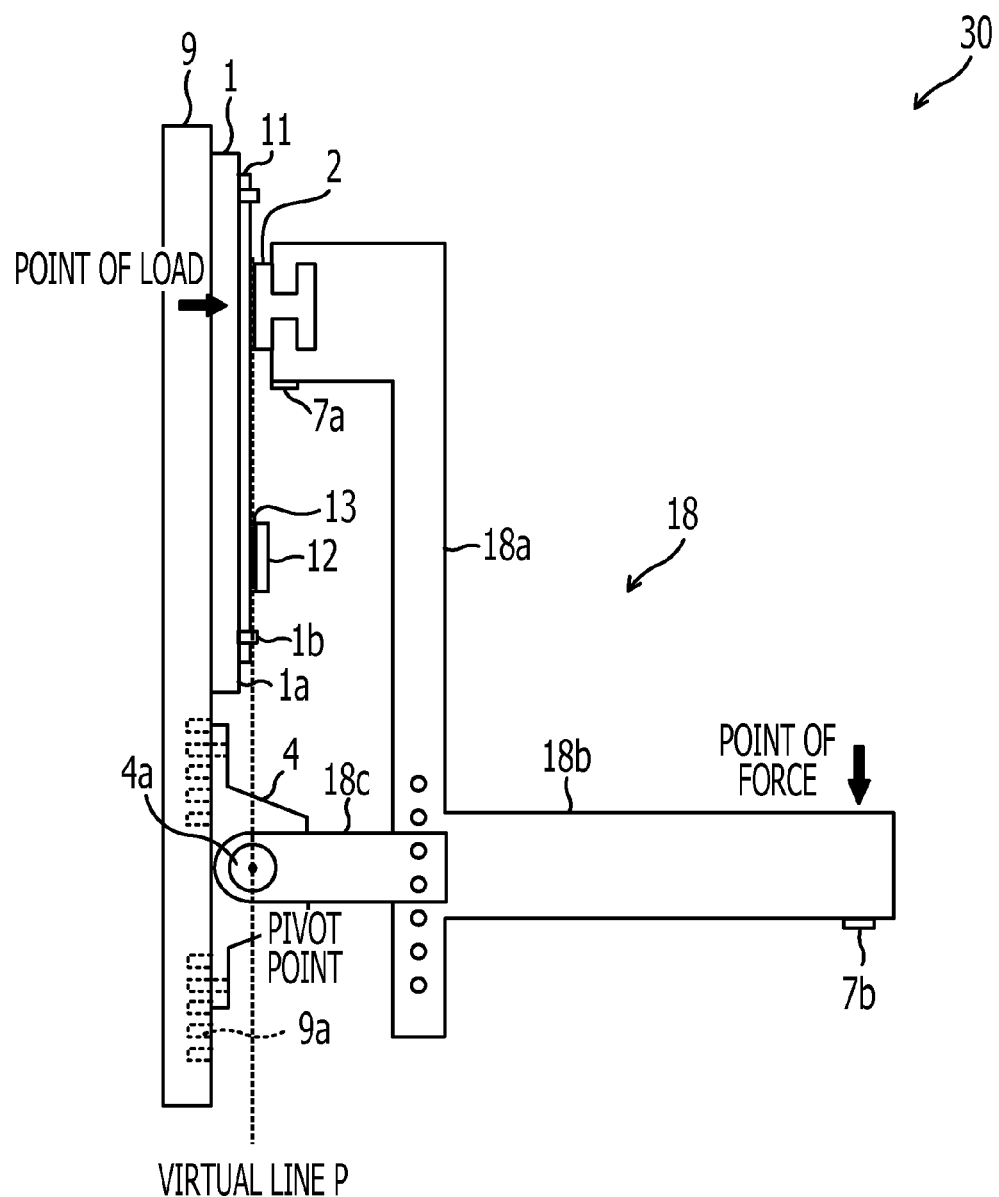
FIG. 7 is a side view of a configuration of an electronic component analyzing apparatus according to Embodiment 3.

An analyzing apparatus 30 in Embodiment 3 is described with reference to FIG. 7. In FIG. 7, the same reference numerals are given to similar elements as those used in Embodiment 1 in FIG. 1A. Also, in FIG. 7, an impact force applying unit is not illustrated for the sake of simplicity. In Embodiment 3, the direction of force transmission to pull off an electronic component 12 is different from that of Embodiment 1. The analyzing apparatus 30 includes a fixing part 1, a gripper 2, a transmission part 18, a support part 4, and the impact force applying unit (not illustrated).

The transmission part 18 includes a first lever 18a, a second lever 18b, and a strut 18c. The first lever 18a is a bar-like member where the gripper 2 is coupled to the upper end portion. The first lever 18a includes a portion extending parallel to the surface of a substrate 11. The second lever 18b is a bar-like member, extending from the lower end portion of the first lever 18a. The second lever 18b is provided perpendicular to the surface of the substrate 11. As illustrated in FIG. 7, the first lever 18a and the second lever 18b may be integrally formed with an L-shape.

The strut 18c supports the first lever 18a and the second lever 18b so that the first lever 18a and the second lever 18b swingably move with respect to the support part 4. A rotation axis 4a is located downward in a vertical direction to the gripper 2. As illustrated in FIG. 7, a virtual line P is drawn so as to extend from the surface of the substrate 11. The virtual line P passes through the gripper 2 and follows the direction in which the external force acts on the transmission part 18. The rotation axis 4a is located on the virtual line P.

The first lever 18a and the second lever 18b of the transmission part 18 correspond to the lever 3a of the transmission part 3 in Embodiment 1. The strut 18c corresponds to the strut 3b in Embodiment 1. Thus, in the analyzing apparatus 30 according to Embodiment 3, the relative position of the pivot point to the point of load is different from that of the analyzing apparatus 10 in Embodiment 1.

When pulling off the electronic component 12 from the substrate 11, the pivot point, the point of force, and the point of load are located respectively in the support part 4, the transmission part 18, and the gripper 2 of the analyzing apparatus 30. That is, the support part 4 functions as a pivot point member, and the transmission part 18 functions as a force point member, and the gripper 2 functions as a load point member.

When impact force is applied to the point of force of the second lever 18b in FIG. 7, the first lever 18a swings about the rotation axis 4a. As illustrated in FIG. 7, since the rotation axis 4a is located downward in a vertical direction to the gripper 2, the direction in which the force acts on the electronic component 12 when pulling off the electronic component 12 from the substrate 11 via the gripper 2, acts only in the X direction, which is approximately perpendicular to the surface of the substrate 11.

Thus, the direction in which the force acts on the electronic component 12 when pulling off the electronic component 12 from the substrate 11 may become perpendicular to the substrate 11, and deformation of the torn surfaces and formation of scratches accompanying a rupture may be reliably suppressed. Thus, the cut surfaces may be analyzed accurately.

The method of applying impact force with the impact force applying unit 5 is not limited to the above-described embodiments. Instead of the drop impact of the steel ball 6, a hydraulic cylinder, an electric motor, or a linear motor may be employed to transmit an instantaneous impact force generated therefrom to the electronic component 12. Likewise, ductile fracture in the solder bumps 13 may be reliably suppressed by increasing the initial velocity of the movement of the gripper 2.

In the above-described embodiments, the method of filling the adhesive 14 in the space between the recess 2f and the electronic component 12 is discussed. However, the electronic component 12 may also be gripped by the gripper 2 without using the adhesive 14. When the adhesive 14 is not used, the shape and size of the recess 2f is desirably formed so that the electronic component 12 fits into the recess 2f (that is, the shape of the recess 2f and the electronic component 12 is desirably formed to be approximately the same). In place of the gripper 2, a gripping structure having a pair of gripping surfaces that separates and comes into contact, and is shaped like tweezers, may be used. To enhance the grip in gripping the electronic component 12, an antislip member including synthetic resin or rubber may be attached to the gripping surfaces, or a groove may be formed by cutting the gripping surface to lock the electronic component 12 inside the groove and prevent the electronic component 12 from falling out.

A shape of the gripper 2 is not limited. When the adhesive 14 is not used, dismounting the electronic component 12 from the gripper 2 after pulling off the electronic component 12 may become easier, and the gripper 2 may become reusable in a shorter time.

The method of adjusting the support location of the transmission part 3 with respect to the support part 4 is not limited to the above-described embodiment in which the plurality of screw holes 3d and 9a, and the plurality of fasteners 21 and 22 are used to achieve an adjustment mechanism. Alternatively, a rail member may be provided over the platform 9, and the support part 4 may slide on the rail member. A fixing mechanism may be also provided to fix the sliding location of the support part 4. Similarly, a rail member and a fixing mechanism may be provided between the upper end portion of the strut 3b and the lever 3a. The amount of force and the direction in which the force acts on the point of load may be set as desired by adjusting the relative position of the pivot point to the point of force and the point of load.

Also, in the above-described embodiments, the torn surfaces of the solder bumps 13 that remain adhered to the electronic component 12 is discussed as the object of observation. Alternatively, the torn surfaces of the solder bumps 13 that remain adhered to the substrate 11 may also be observed, or the torn surfaces of the solder bumps 13 that remain adhered to the electronic component 12 and the substrate 11 may both be observed.

Also, the electronic component to be pulled off is not limited to the BGA package discussed in the above-described embodiments. For example, a small outline package (SOP) or a quad flat package (QFP) with leads extending from lateral sides thereof may be employed. In case of SOP or QFP, the solder joint may be torn off by hardening the leads with the adhesive 14. On the other hand, among surface mount packages, a chip size package (CSP) or a Super CSP (SCSP) may be also employed.

Although the embodiments of the present invention are numbered with, for example, "1," "2," or "3," the ordinal numbers do not imply priorities of the embodiments. Many other variations and modifications will be apparent to those skilled in the art.

All examples and conditional language recited herein are intended for pedagogical purposes to aid the reader in understanding the invention and the concepts contributed by the inventors to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

What is claimed is:

1. An electronic component analyzing apparatus, said apparatus comprising:
   a fixing part configured to hold a substrate to which an electronic component is soldered;
   a gripper configured to grip the electronic component;
   a transmission part coupled to the gripper, and configured to transmit an external force to the gripper as a force acting in a direction away from the substrate, wherein the transmission part includes:
- a swinging part configured to swing about the support part in response to the external force;
- a movement conversion part configured to convert a swing movement of the swinging part into a rectilinear movement in a direction perpendicular to the substrate; and
- a rectilinear movement member coupled to the swinging part via the movement conversion part, wherein the gripper is provided on one end of the rectilinear movement member such that the electronic component is pulled off from the substrate in the direction perpendicular to the substrate; and
- a support part configured to pivotally support the transmission part.

2. The electronic component analyzing apparatus according to claim 1, wherein the gripper is removably provided on the transmission part.

3. The electronic component analyzing apparatus according to claim 1, further comprising an adjustment mechanism configured to adjust a support location of the support part with respect to the transmission part.

4. The electronic component analyzing apparatus according to claim 1, further comprising a guide member configured to slidingly guide the rectilinear movement member.

5. The electronic component analyzing apparatus according to claim 1, further comprising a first sensor provided in a vicinity of the gripper, and configured to detect an acceleration acting on the electronic component.

6. The electronic component analyzing apparatus according to claim 1, further comprising a second sensor provided on the transmission part, and configured to detect an acceleration caused by the external force.

7. The electronic component analyzing apparatus according to claim 1, further comprising a first adhesion layer provided between a back surface of the electronic component and the gripper.

8. The electronic component analyzing apparatus according to claim 1, further comprising a second adhesion layer provided between a side surface of the electronic component and the gripper.

9. The electronic component analyzing apparatus according to claim 1, further comprising an impact force applying unit configured to generate the external force and apply an instantaneous impact force to the transmission part.

10. The electronic component analyzing apparatus according to claim 1, wherein the support part includes a rotation axis which is located on a virtual line extending from a surface of the substrate.

11. An electronic component analyzing method, comprising:
- holding, with a fixing part, a substrate to which an electronic component is soldered;
- gripping the electronic component with a gripper;
- transmitting an external force to the gripper via a transmission part; and
- pivotally supporting the transmission part, wherein a swing movement of the transmission part is converted into a rectilinear movement in a direction perpendicular to the substrate.

12. The electronic component analyzing method according to claim 11, wherein a support location of the transmission part is adjusted with respect to the fixing part.

13. The electronic component analyzing method according to claim 11, wherein the transmission part is slidingly supported by a guide member.

14. The electronic component analyzing method according to claim 11, further comprising detecting an acceleration acting on the electronic component using a first sensor.

15. The electronic component analyzing method according to claim 11, further comprising detecting an acceleration caused by the external force using a second sensor.

16. The electronic component analyzing method according to claim 11, further comprising bonding a back surface of the electronic component to the gripper.

17. The electronic component analyzing method according to claim 11, further comprising applying an instantaneous impact force from the external force to the transmission part.

18. The electronic component analyzing method according to claim 11, wherein a rotation axis about which the transmission part swings is located on a virtual line extending from a surface of the substrate.

* * * * *